US009862981B2

(12) United States Patent
Thompson et al.

(10) Patent No.: US 9,862,981 B2
(45) Date of Patent: Jan. 9, 2018

(54) THERMOPHILIC ACETYLXYLAN ESTERASE GENES AND ENZYMES FROM ALICYCLOBACILLUS ACIDOCALDARIUS AND RELATED ORGANISMS AND METHODS

(71) Applicant: BATTELLE ENERGY ALLIANCE, LLC, Idaho Falls, ID (US)

(72) Inventors: Vicki S Thompson, Idaho Falls, ID (US); David N Thompson, Idaho Falls, ID (US); David W Reed, Idaho Falls, ID (US); Jeffrey A Lacey, Idaho Falls, ID (US); William A Apel, Jackson, WY (US)

(73) Assignee: BATTELLE ENERGY ALLIANCE, LLC, Idaho Falls, ID (US)

( * ) Notice: Subject to any disclaimer, the term of this patent is extended or adjusted under 35 U.S.C. 154(b) by 0 days.

(21) Appl. No.: 15/152,304

(22) Filed: May 11, 2016

(65) Prior Publication Data

US 2017/0327856 A1 Nov. 16, 2017

(51) Int. Cl.
C12Q 1/44 (2006.01)
C12P 19/06 (2006.01)
C12N 9/18 (2006.01)

(52) U.S. Cl.
CPC ............. *C12P 19/06* (2013.01); *C12N 9/18* (2013.01); *C12Y 301/01072* (2013.01)

(58) Field of Classification Search
CPC ................................................... C12N 15/52

USPC ............................................. 435/19, 200, 209
See application file for complete search history.

(56) References Cited

U.S. PATENT DOCUMENTS 8,969,033 B2 * 3/2015 Thompson ........... C12N 9/1048
435/200

* cited by examiner

Primary Examiner — Tekchand Saidha
(74) Attorney, Agent, or Firm — TraskBritt

(57) ABSTRACT

A genetically modified organism comprising at least one nucleic acid sequence and/or at least one recombinant nucleic acid isolated from *Alicyclobacillus acidocaldarius* and encoding a polypeptide involved in at least partially degrading, cleaving, transporting, metabolizing, or removing polysaccharide, lignocellulose, hemicellulose, lignin, chitin, heteroxylan, and/or xylan-decorating group; and at least one nucleic acid sequence and/or at least one recombinant nucleic acid encoding a polypeptide involved in fermenting sugar molecules to a product. Additionally, enzymatic and/or proteinaceous extracts may be isolated from one or more genetically modified organisms. The extracts are utilized to convert biomass into a product. Further provided are methods of converting biomass into products comprising: placing the genetically modified organism and/or enzymatic extracts thereof in fluid contact with polysaccharides, cellulose, lignocellulose, hemicellulose, lignin, starch, sugars, sugar oligomers, carbohydrates, complex carbohydrates, chitin, heteroxylans, glycosides, and/or xylan-, glucan-, galactan-, or mannan-decorating groups.

10 Claims, 2 Drawing Sheets

FIGURE 1

```
gi|944285589|gb|KQL49232.1|        ------MERSTP-ISRRPKAVALTFDDGPDQIWTPRILDVLADYRIHATFMCVGKAVQRN
gi|916736932|ref|WP_051343988.1|   MQTDAQ---SRVVRRIDRPTLTLTFDDGPDADYTPQILAILHHYSVSATFFCLGQQIDQC
SeqIdNo:2                          MKEDLRLQRQTPEPSSPPRHLAITFDDGPDGDMTPKILSTLRDYGVPATFFCIGQQVERF
gi|917405684|ref|WP_052012396.1|   ----MDNSRTRQQTPARVGTLTITFDDGPDAEYTPQILETLRHYGVPAVFFCIGEQVARY
gi|954102927|gb|KRW91354.1|        ------------MTITFDDGPDAEYTPKILETLRHYGVPAVFFCIGEQVARY
gi|955294285|ref|WP_058095214.1|   ----MDNSRTRQQTPARVGHLTITFDDGPDAEYTPKILETLRHYGVPAVFFCIGEQVARY
                                               :: ********  **:** * .*.*:*:*::  :.

gi|944285589|gb|KQL49232.1|        PQMLRRIKDEGHIIGNHTWDHPNLTQLPLSDVQTQVLRTTEEIDRVAGVKTRLFRPPYGD
gi|916736932|ref|WP_051343988.1|   PHILKQIAAAGHTVGNHSYSHPNLITEITSGEVLKQMTETDERIANELGSRPRWMRPPYGA
SeqIdNo:2                          PDVLKSIHQAGHEIGNHTMTHPYLTKLTDAEIERELRECQAAIEKVVQVPIRYFRPPYGD
gi|917405684|ref|WP_052012396.1|   PDVLRAIDAAGHAIGNHTMTHPHLTELPDDEIRKQLTDAANQIEATIGKRPHLFRPPYGD
gi|954102927|gb|KRW91354.1|        PDVLRAIDAAGHAVGNHTMTHPHLTELPDDEIRKQLTDAANQIEATIGKRPHLFRPPYGD
gi|955294285|ref|WP_058095214.1|   PDVLRAIDAAGHAVGNHTMTHPHLTELPDDEIRKQLTDAANQIEATIGKRPHLFRPPYGD
                                   *.:*: *   :*.  ::       ::         *       :****** gi|944285589|gb|KQL49232.1|        LNDDIVRKVTSLDHEILLWDIDSWDWKGLTGPQVAKNILGHVRDGSIVLQHCAGPTETVK
gi|916736932|ref|WP_051343988.1|   INENVKAQLQELGYEIILWDIDSRDWAGIPGPQIARNILSQLKPGAIILQHCSK---SAA
SeqIdNo:2                          IDDRVRRIAASLHYEVLWDVDSLDWSGIPGPAVAANVLPKLRPGAIILMHAGP---FAK
gi|917405684|ref|WP_052012396.1|   MDERVERIARELGYQPVLWDVDSVDWSGIPGPTVAANVLPHLKPGAIVLQHAGE---HAE
gi|954102927|gb|KRW91354.1|        MDDRVERIARELGYQPVLWDVDSVDWSGIPGPTVAANVLPHLKPGAIVLQHAGG---HAQ
gi|955294285|ref|WP_058095214.1|   MDDRVERIARELGYQPVLWDVDSVDWSGIPGPTVAANVLPHLKPGAIVLQHAGG---HAQ
                                   :::.: .   ::    :::    *: ** :*: :::: *:* gi|944285589|gb|KQL49232.1|        GTLEALPYIIEVLSESGFTFSTIPQLLHLSAYR-
gi|916736932|ref|WP_051343988.1|   GTVEALPYVIEIALGLGYEFTTLDALLGQSPYQD
SeqIdNo:2                          GTPEALPVLEVAVAMGYDFVPLAKLHR------
gi|917405684|ref|WP_052012396.1|   GTPAALPYIIEVAVAMGYDWVPFTSKS------
gi|954102927|gb|KRW91354.1|        GTPAALPYIIEVAVAMGYDWVPFTSKS------
gi|955294285|ref|WP_058095214.1|   GTPAALPYIIEVAVAMGYDWVPFTSKS------
                                   **  *****::*:*    *:*       ::
```

THERMOPHILIC ACETYLXYLAN ESTERASE GENES AND ENZYMES FROM ALICYCLOBACILLUS ACIDOCALDARIUS AND RELATED ORGANISMS AND METHODS

GOVERNMENT RIGHTS

This invention was made with government support under Contract Number DE-AC07-99ID13727 and Contract Number DE-AC07-05ID14517 awarded by the United States Department of Energy. The government has certain rights in the invention.

STATEMENT ACCORDING TO 37 C.F.R. §1.821(c) or (e)—SEQUENCE LISTING SUBMITTED AS A TXT AND PDF FILES

Pursuant to 37 C.F.R. §1.821(c) or (e), files containing a TXT version and a PDF version of the Sequence Listing have been submitted concomitant with this application, the contents of which are hereby incorporated by reference.

BACKGROUND

Dilute acid hydrolysis to remove hemicellulose from lignocellulosic materials is one of the most developed pretreatment techniques for lignocellulose and is currently favored (Hamelinck et al., 2005) because it results in fairly high yields of xylose (75% to 90%). Conditions that are typically used range from 0.1 to 1.5% sulfuric acid and temperatures above 160° C. The high temperatures used result in significant levels of thermal decomposition products that inhibit subsequent microbial fermentations (Lavarack et al., 2002). High temperature hydrolysis requires pressurized systems, steam generation, and corrosion resistant materials in reactor construction due to the more corrosive nature of acid at elevated temperatures.

Lower temperature acid hydrolyses are of interest because they have the potential to overcome several of the above shortcomings (Tsao et al., 1987). It has been demonstrated that 90% of hemicellulose can be solubilized as oligomers in a few hours of acid treatment in the temperature range of 80° C. to 100° C. It has also been demonstrated that the sugars produced in low temperature acid hydrolysis are stable under those same conditions for at least 24 hours with no detectable degradation to furfural decomposition products. Finally, sulfuric acid typically used in pretreatments is not as corrosive at lower temperatures. The use of lower temperature acid pretreatments requires much longer reaction times to achieve acceptable levels of hydrolysis. Although 90% hemicellulose solubilization has been shown (Tsao, 1987), the bulk of the sugars are in the form of oligomers and are not in the monomeric form. The organisms currently favored in subsequent fermentation steps cannot utilize sugar oligomers (Garrote et al., 2001) and the oligomer-containing hydrolysates require further processing to monomers, usually as a second acid or alkaline hydrolysis step (Garrote et al., 2001).

Other acidic pretreatment methods include autohydrolysis and hot water washing. In autohydrolysis, biomass is treated with steam at high temperatures (~240° C.), which cleaves acetyl side chains associated with hemicellulose to produce acetic acid that functions in a similar manner to sulfuric acid in acid hydrolysis. Higher pretreatment temperatures are required as compared to dilute sulfuric acid hydrolysis because acetic acid is a much weaker acid than sulfuric. At temperatures below 240° C., the hemicellulose is not completely hydrolyzed to sugar monomers and has high levels of oligomers (Garrote et al., 2001). In hot water washing, biomass is contacted with water (under pressure) at elevated temperatures 160° C. to 220° C. This process can effectively hydrolyze greater than 90% of the hemicellulose present, and the solubilized hemicellulose was typically over 95% in the form of oligomers (Liu and Wyman, 2003).

BRIEF SUMMARY

Embodiments relate to a nucleotide sequence of the genome of *Alicyclobacillus acidocaldarius*, or a homologue or fragment thereof, in combination with at least one sequence that is heterologous to *Alicyclobacillus acidocaldarius*. In one embodiment, the nucleotide sequence is SEQ ID No. 1 or a homologue or fragment thereof. In another embodiment, the nucleotide sequence has at least 90% sequence identity to SEQ ID No. 1.

Embodiments may further relate to an isolated and/or purified nucleic acid sequence comprising a nucleic acid sequence encoding a polypeptide selected from the group consisting of a polypeptide having at least 90% sequence identity to SEQ ID No. 2, the nucleic acid sequence in combination with at least one sequence that is heterologous to *Alicyclobacillus acidocaldarius*.

Embodiments also relate to the use of isolated and/or purified polypeptides encoded by a nucleotide sequence of the genome of *Alicyclobacillus acidocaldarius*, or a homologue or fragment thereof. In one embodiment, the polypeptide is SEQ ID No. 2 or a homologue or fragment thereof. In another embodiment, the polypeptide has at least 90% sequence identity to SEQ ID No. 2. In these and other embodiments, the polypeptide has activity as an acetyxylan esterase.

In embodiments, the polypeptides may be acidophilic and/or thermophilic. In further embodiments, the polypeptides may be glycosylated, pegylated, and/or otherwise post-translationally modified.

Embodiments include methods of at least partially degrading, cleaving, or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups. Such methods may comprise placing a polypeptide having at least 90% sequence identity to SEQ ID No. 2 in fluid contact with a polysaccharide, lignocellulose, cellulose, hemicellulose, lignin, starch, chitin, polyhydroxybutyrate, heteroxylan, glycoside, xylan-, glucan-, galactan-, and/or mannan-decorating group.

These and other aspects of the disclosure will become apparent to the skilled artisan in view of the teachings contained herein.

BRIEF DESCRIPTION OF THE DRAWINGS

FIG. 1 depicts a sequence alignment between SEQ ID NO:2 (RAAC02760), an acetylxylan esterase, and gi|944285589, gi|916736932, gi|917405684, gi|954102927, and gi|955294285 (SEQ ID NOs:3-7 respectively) which are all esterases. Amino acids common to all of the sequences are indicated by a "*", while amino acids with only conservative substitutions are indicated by ":".

DETAILED DESCRIPTION

Figure 2:
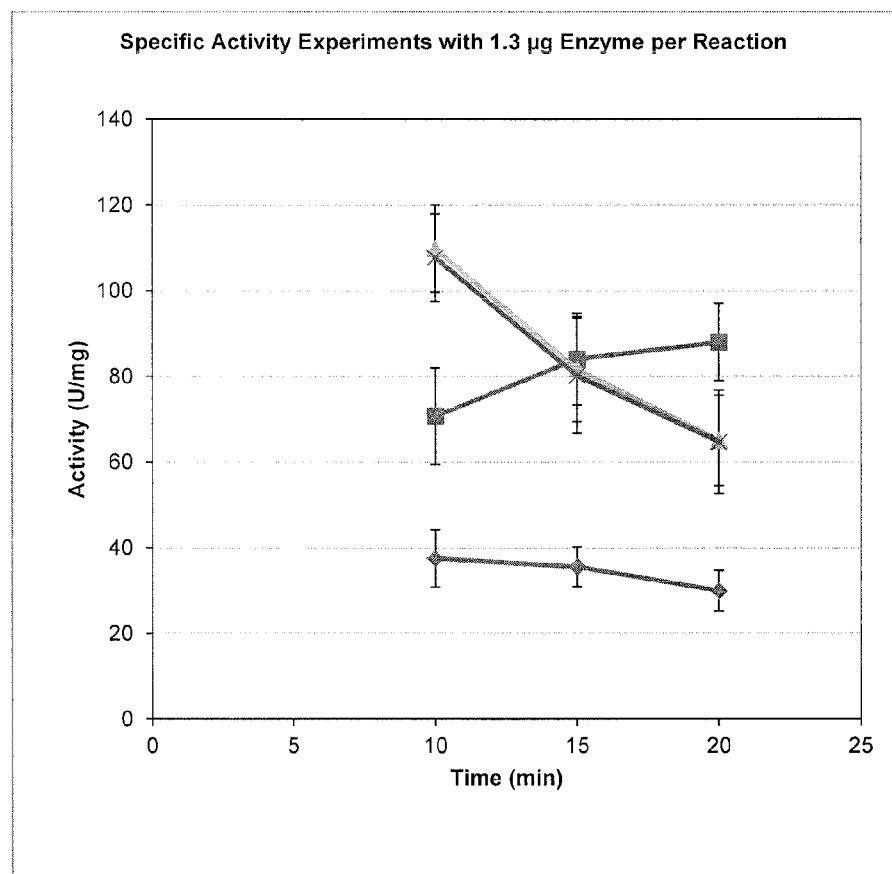
FIG. 2 depicts a representation of the activity of four different preparations (represented as Xs, triangles, squares, and diamonds) of SEQ ID NO: 2. Therein, the activity (units/mg) as an acetylxylan esterase is shown at 10, 15, and 20 minutes.

Lignocellulose is a highly heterogeneous three-dimensional matrix comprised of cellulose, hemicellulose, and lignin. Many fuels and chemicals can be made from these lignocellulosic materials. To utilize lignocellulosic biomass for production of fuels and chemicals via fermentative processes, it is necessary to convert the plant polysaccharides to simpler sugars, which are then fermented to products using a variety of organisms. Direct hydrolysis of cellulose by mineral acids to monomers is possible at high temperature and pressure, leading to yield losses due to thermal decomposition of the sugars. One strategy to reduce these yield losses is to use cellulases and potentially other enzymes to depolymerize the polysaccharides at moderate temperatures. Addition of acid-stable thermotolerant hydrolytic enzymes such as cellulases and xylanases to the biomass slurry during the pretreatment enables the use of lower temperatures and pressures, as well as cheaper materials of reactor construction, reducing both the capital and energy costs. Another approach is to combine the reduced severity pretreatment with enzymes together with fermentation under the same conditions, using a single organism that produces the enzymes to degrade the material as well as ferment the sugars to the value-added product of choice.

For commercially available enzymes to be used for this purpose, the pretreatment slurry must be neutralized and cooled to 40° C. to 50° C., adding significant cost to the process. Hence, it would be an improvement in the art to degrade the soluble oligomers produced using acid, autohydrolysis or hot water washing pretreatments, at reduced severity and without neutralization using, for example, thermophilic and/or acidophilic enzymes.

Embodiments of the disclosure relate in part to the gene sequences and protein sequences encoded by genes of *Alicyclobacillus acidocaldarius*. Of particular interest for polysaccharide depolymerization are esterases including acetylxylan esterases. In embodiments, the acetylxylan esterases may be thermophilic and/or acidophilic.

The present disclosure relates to isolated and/or purified nucleotide sequences of the genome of *Alicyclobacillus acidocaldarius* including SEQ ID No. 1 or fragments thereof. In embodiments, these sequences may be in combination with at least one sequence that is heterologous to *Alicyclobacillus acidocaldarius*.

The present disclosure likewise relates to isolated and/or purified nucleotide sequences, characterized in that they are selected from: a) a nucleotide sequence of a specific fragment of the sequence SEQ ID No. 1; b) a nucleotide sequence homologous to a nucleotide sequence such as defined in a); c) a nucleotide sequence complementary to a nucleotide sequence such as defined in a) or b), and a nucleotide sequence of their corresponding RNA; d) a nucleotide sequence capable of hybridizing under stringent conditions with a sequence such as defined in a), b) or c); e) a nucleotide sequence comprising a sequence such as defined in a), b), c) or d); and f) a nucleotide sequence modified by a nucleotide sequence such as defined in a), b), c), d) or e).

Nucleotide, polynucleotide, or nucleic acid sequence will be understood according to the present disclosure as meaning both a double-stranded or single-stranded DNA in the monomeric and dimeric (so-called "in tandem") forms and the transcription products of said DNAs.

In embodiments, the sequences described herein may be in combination with heterologous sequences. As used herein, "heterologous sequence" refers to sequences which are either artificial (not found in nature) as well as sequences that are not found in *Alicyclobacillus acidocaldarius* directly connected to the sequences from *Alicyclobacillus acidocaldarius* described herein. Thus, any sequence, when added to a sequence from *Alicyclobacillus acidocaldarius*, creates, as a whole, a sequence that is not found in *Alicyclobacillus acidocaldarius*, is a "heterologous sequence." Examples of heterologous sequences include, but are not limited to, promoters, enhancers, tags, terminators, and hairpins that are not operatively linked to the sequence from *Alicyclobacillus acidocaldarius* as found in nature.

Aspects of the disclosure relate to nucleotide sequences which it has been possible to isolate, purify or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning, and subcloning, it being possible for the sequences of the invention to be carried by vectors.

Isolated and/or purified nucleotide sequence fragment according to the disclosure will be understood as designating any nucleotide fragment of the genome of *Alicyclobacillus acidocaldarius*, and may include, by way of non-limiting example, length of at least 8, 12, 20, 25, 50, 75, 100, 200, 300, 400, 500, 1000, or more, consecutive nucleotides of the sequence from which it originates.

Specific fragment of an isolated and/or purified nucleotide sequence according to the disclosure will be understood as designating any nucleotide fragment of the genome of *Alicyclobacillus acidocaldarius*, having, after alignment and comparison with the corresponding fragments of genomic sequences of *Alicyclobacillus acidocaldarius*, at least one nucleotide or base of different nature.

Homologous isolated and/or purified nucleotide sequence in the sense of the present disclosure is understood as meaning isolated and/or purified a nucleotide sequence having at least a percentage identity with the bases of a nucleotide sequence according to the invention of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%, this percentage being purely statistical and it being possible to distribute the differences between the two nucleotide sequences at random and over the whole of their length.

Specific homologous nucleotide sequence in the sense of the present disclosure is understood as meaning a homologous nucleotide sequence having at least one nucleotide sequence of a specific fragment, such as defined above. Said "specific" homologous sequences can comprise, for example, the sequences corresponding to the genomic sequence or to the sequences of its fragments representative of variants of the genome of *Alicyclobacillus acidocaldarius*. These specific homologous sequences can thus correspond to variations linked to mutations within strains of *Alicyclobacillus acidocaldarius*, and especially correspond to truncations, substitutions, deletions and/or additions of at least one nucleotide. Said homologous sequences can likewise correspond to variations linked to the degeneracy of the genetic code.

The term "degree or percentage of sequence homology" refers to "degree or percentage of sequence identity between two sequences after optimal alignment" as defined in the present application.

Two amino-acids or nucleotidic sequences are said to be "identical" if the sequence of amino-acids or nucleotidic residues, in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, *Ad. App. Math* 2: 482 (1981), by the homology alignment algorithm of Neddleman and Wunsch, *J. Mol. Biol.* 48: 443 (1970), by the search for similarity method of Pearson and Lipman, *Proc. Natl. Acad. Sci.* (U.S.A.) 85: 2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

"Percentage of sequence identity" (or degree of identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

The definition of sequence identity given above is the definition that would be used by one of skill in the art. The definition by itself does not need the help of any algorithm, said algorithms being helpful only to achieve the optimal alignments of sequences, rather than the calculation of sequence identity.

From the definition given above, it follows that there is a well-defined and only one value for the sequence identity between two compared sequences which value corresponds to the value obtained for the best or optimal alignment.

In the BLAST N or BLAST P "BLAST 2 sequence," software which is available in the web site www.ncbi.nlm.nih.gov/gorf/bl2.html, and habitually used by the inventors and in general by the skilled person for comparing and determining the identity between two sequences, gap cost which depends on the sequence length to be compared is directly selected by the software (i.e., 11.2 for substitution matrix BLOSUM-62 for length>85).

Complementary nucleotide sequence of a sequence of the disclosure is understood as meaning any DNA whose nucleotides are complementary to those of the sequence of the disclosure, and whose orientation is reversed (antisense sequence).

Hybridization under conditions of stringency with a nucleotide sequence according to the disclosure is understood as meaning hybridization under conditions of temperature and ionic strength chosen in such a way that they enable the maintenance of the hybridization between two fragments of complementary DNA.

By way of illustration, conditions of great stringency of the hybridization step with the aim of defining the nucleotide fragments described above are advantageously the following.

The hybridization is carried out at a preferential temperature of 65° C. in the presence of SSC buffer, 1×SSC corresponding to 0.15 M NaCl and 0.05 M Na citrate. The washing steps, for example, can be the following: 2×SSC, at ambient temperature followed by two washes with 2×SSC, 0.5% SDS at 65° C.; 2×0.5×SSC, 0.5% SDS; at 65° C. for 10 minutes each.

The conditions of intermediate stringency, using, for example, a temperature of 42° C. in the presence of a 2×SSC buffer, or of less stringency, for example, a temperature of 37° C. in the presence of a 2×SSC buffer, respectively, require a globally less significant complementarity for the hybridization between the two sequences.

The stringent hybridization conditions described above for a polynucleotide with a size of approximately 350 bases will be adapted by the person skilled in the art for oligonucleotides of greater or smaller size, according to the teaching of Sambrook et al., 1989.

Among the isolated and/or purified nucleotide sequences according to the disclosure, are those which can be used as a primer or probe in methods enabling the homologous sequences according to the disclosure to be obtained, these methods, such as the polymerase chain reaction (PCR), nucleic acid cloning, and sequencing, being well known to the person skilled in the art.

Among said isolated and/or purified nucleotide sequences according to the disclosure, those are again preferred which can be used as a primer or probe in methods enabling the presence of SEQ ID No. 1, one of its fragments, or one of its variants such as defined below to be diagnosed.

The nucleotide sequence fragments according to the disclosure can be obtained, for example, by specific amplification, such as PCR, or after digestion with appropriate restriction enzymes of nucleotide sequences according to the invention, these methods in particular being described in the work of Sambrook et al., 1989. Such representative fragments can likewise be obtained by chemical synthesis according to methods well known to persons of ordinary skill in the art.

"Modified nucleotide sequence" will be understood as meaning any nucleotide sequence obtained by mutagenesis according to techniques well known to the person skilled in the art, and containing modifications with respect to the normal sequences according to the disclosure, for example, mutations in the regulatory and/or promoter sequences of polypeptide expression, especially leading to a modification of the rate of expression of said polypeptide or to a modulation of the replicative cycle.

"Modified nucleotide sequence" will likewise be understood as meaning any nucleotide sequence coding for a modified polypeptide such as defined below.

Embodiments of the disclosure likewise relate to isolated and/or purified nucleotide sequences characterized in that they comprise a nucleotide sequence selected from: a) the nucleotide sequence of SEQ ID No. 1, or one of its fragments; b) a nucleotide sequence of a specific fragment of a sequence such as defined in a); c) a homologous nucleotide sequence having at least 90% identity with a sequence such as defined in a) or b); d) a complementary nucleotide sequence or sequence of RNA corresponding to a sequence such as defined in a), b) or c); and e) a nucleotide sequence modified by a sequence such as defined in a), b), c) or d).

Among the isolated and/or purified nucleotide sequences according to the disclosure are the nucleotide sequences of SEQ ID Nos. 8-12, or fragments thereof and any other isolated and/or purified nucleotide sequences which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with the sequence SEQ ID No. 1 or fragments thereof. Said homologous sequences can comprise, for example, the sequences corresponding to the genomic sequences *Alicyclobacillus acidocaldarius*. In the same manner, these specific homologous sequences can correspond to variations linked to mutations within strains of *Alicyclobacillus acidocaldarius* and especially correspond to truncations, substitutions, deletions and/or additions of at least one nucleotide.

Embodiments of the disclosure comprise the isolated and/or purified polypeptides encoded by a nucleotide sequence according to the disclosure, or fragments thereof, whose sequence is represented by a fragment. Amino acid sequences corresponding to the isolated and/or purified polypeptides can be encoded according to one of the three possible reading frames of the sequence of SEQ ID No. 1.

Embodiments of the disclosure likewise relate to the isolated and/or purified polypeptides, characterized in that they comprise the polypeptide of SEQ No. 2, or one of its fragments.

Among the isolated and/or purified polypeptides, according to embodiments of the disclosure, are the isolated and/or purified polypeptides of the amino acid sequences of SEQ ID Nos. 13-17, or fragments thereof or any other isolated and/or purified polypeptides which have a homology of at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% identity with the sequence of SEQ ID No. 2, or fragments thereof.

Embodiments of the disclosure also relate to the polypeptides, characterized in that they comprise a polypeptide selected from: a) a specific fragment of at least 5 amino acids of a polypeptide of an amino acid sequence according to the invention; b) a polypeptide homologous to a polypeptide such as defined in a); c) a specific biologically active fragment of a polypeptide such as defined in a) or b); and d) a polypeptide modified by a polypeptide such as defined in a), b) or c).

In the present description, the terms polypeptide, peptide and protein are interchangeable.

In embodiments of the disclosure, the isolated and/or purified polypeptides according to the disclosure may be glycosylated, pegylated, and/or otherwise post-translationally modified. In further embodiments, glycosylation, pegylation, and/or other post-translational modifications may occur in vivo or in vitro and/or may be performed using chemical techniques. In additional embodiments, any glycosylation, pegylation and/or other post-translational modifications may be N-linked or O-linked.

In embodiments of the disclosure any one of the isolated and/or purified polypeptides according to the disclosure may be enzymatically active at temperatures at or above about 25, 30, 35, 40, 45, 50, 55, 60, 65, 70, 75, 80, 85, 90, and/or 95 degrees Celsius and/or may be enzymatically active at a pH at, below, and/or above 7, 6, 5, 4, 3, 2, 1, and/or 0. In further embodiments of the disclosure, glycosylation, pegylation, and/or other post-translational modification may be required for the isolated and/or purified polypeptides according to the disclosure to be enzymatically active at pH at or below 7, 6, 5, 4, 3, 2, 1, and/or 0 or at temperatures at or above about 25, 30, 35, 40, 45, 50, 55, 60, 65, 70, 75, 80, 85, 90, and/or 95 degrees Celsius.

Aspects of the disclosure relate to polypeptides that are isolated or obtained by purification from natural sources, or else obtained by genetic recombination, or alternatively by chemical synthesis and that they may thus contain unnatural amino acids, as will be described below.

A "polypeptide fragment" according to the embodiments of the disclosure is understood as designating a polypeptide containing at least 5 consecutive amino acids, preferably 10 consecutive amino acids or 15 consecutive amino acids.

In the present disclosure, a specific polypeptide fragment is understood as designating the consecutive polypeptide fragment encoded by a specific fragment nucleotide sequence according to the invention.

"Homologous polypeptide" will be understood as designating the polypeptides having, with respect to the natural polypeptide, certain modifications such as, in particular, a deletion, addition, or substitution of at least one amino acid, a truncation, a prolongation, a chimeric fusion, and/or a mutation. Among the homologous polypeptides, those are preferred whose amino acid sequence has at least 80% or 90%, homology with the sequences of amino acids of polypeptides according to the disclosure.

"Specific homologous polypeptide" will be understood as designating the homologous polypeptides such as defined above and having a specific fragment of polypeptide according to the disclosure.

In the case of a substitution, one or more consecutive or nonconsecutive amino acids are replaced by "equivalent" amino acids. The expression "equivalent" amino acid is directed here at designating any amino acid capable of being substituted by one of the amino acids of the base structure without, however, essentially modifying the biological activities of the corresponding peptides and such that they will be defined by the following. Examples of such substitutions in the amino acid sequence of SEQ ID No. 2 may include those isolated and/or purified polypeptides of the amino acid sequences of SEQ ID Nos. 13-17.

These equivalent amino acids can be determined either by depending on their structural homology with the amino acids which they substitute, or on results of comparative tests of biological activity between the different polypeptides, which are capable of being carried out.

By way of nonlimiting example, the possibilities of substitutions capable of being carried out without resulting in an extensive modification of the biological activity of the corresponding modified polypeptides will be mentioned, the replacement, for example, of leucine by valine or isoleucine, of aspartic acid by glutamic acid, of glutamine by asparagine, of arginine by lysine etc., the reverse substitutions naturally being envisageable under the same conditions.

In a further embodiment, substitutions are limited to substitutions in amino acids not conserved among other proteins which have similar identified enzymatic activity. For example, the figures herein provide sequence alignments between certain polypeptides of the disclosure and other polypeptides identified as having similar enzymatic activity, with amino acids common to three or more of the sequences aligned as indicated in bold. Thus, according to one embodiment of the disclosure, substitutions or mutations may be made at positions that are not indicated as in bold in figures. Examples of such polypeptides may include, but are not limited to, those found in the amino acid sequences of SEQ ID Nos. 13-17. In a further embodiment, nucleic acid sequences may be mutated or substituted such that the amino acid they encode is unchanged (degenerate substitutions and/or mutations) and/or mutated or substituted such that any resulting amino acid substitutions or mutations are made at positions that are not indicated as in bold in figures. Examples of such nucleic acid sequences may include, but are not limited to, those found in the nucleotide sequences of SEQ ID Nos. 13-17 or fragments thereof.

The specific homologous polypeptides likewise correspond to polypeptides encoded by the specific homologous nucleotide sequences, such as defined above, and thus comprise in the present definition polypeptides which are mutated or correspond to variants which can exist in *Alicyclobacillus acidocaldarius*, and which especially correspond to truncations, substitutions, deletions, and/or additions of at least one amino acid residue.

"Specific biologically active fragment of a polypeptide," according to an embodiment of the disclosure will be understood in particular as designating a specific polypeptide fragment, such as defined above, having at least one of the characteristics of polypeptides according to the disclosure. In certain embodiments the peptide is capable of acting as an Acetylxylan esterase.

The polypeptide fragments according to embodiments of the disclosure can correspond to isolated or purified fragments naturally present in a *Alicyclobacillus acidocaldarius* or correspond to fragments which can be obtained by cleavage of said polypeptide by a proteolytic enzyme, such as trypsin or chymotrypsin or collagenase, or by a chemical reagent, such as cyanogen bromide (CNBr). Such polypeptide fragments can likewise just as easily be prepared by chemical synthesis, from hosts transformed by an expression vector according to the disclosure containing a nucleic acid enabling the expression of said fragments, placed under the control of appropriate regulation and/or expression elements.

"Modified polypeptide" of a polypeptide according to an embodiment of the disclosure is understood as designating a polypeptide obtained by genetic recombination or by chemical synthesis as will be described below, having at least one modification with respect to the normal sequence. These modifications may or may not be able to bear on amino acids at the origin of specificity, and/or of activity, or at the origin of the structural conformation, localization, and of the capacity of membrane insertion of the polypeptide according to the disclosure. It will thus be possible to create polypeptides of equivalent, increased, or decreased activity, and of equivalent, narrower, or wider specificity. Among the modified polypeptides, it is necessary to mention the polypeptides in which up to 5 amino acids can be modified, truncated at the N- or C-terminal end, or even deleted or added.

The methods enabling said modulations on eukaryotic or prokaryotic cells to be demonstrated are well known to the person of ordinary skill in the art. It is likewise well understood that it will be possible to use the nucleotide sequences coding for said modified polypeptides for said modulations, for example, through vectors according to the disclosure and described below.

The preceding modified polypeptides can be obtained by using combinatorial chemistry, in which it is possible to systematically vary parts of the polypeptide before testing them on models, cell cultures or microorganisms, for example, to select the compounds which are most active or have the properties sought.

Chemical synthesis likewise has the advantage of being able to use unnatural amino acids, or nonpeptide bonds.

Thus, in order to improve the duration of life of the polypeptides according to the disclosure, it may be of interest to use unnatural amino acids, for example, in D form, or else amino acid analogs, especially sulfur-containing forms, for example.

Finally, it will be possible to integrate the structure of the polypeptides according to the disclosure, its specific or modified homologous forms, into chemical structures of polypeptide types or others. Thus, it may be of interest to provide at the N- and C-terminal ends compounds not recognized by proteases.

The nucleotide sequences coding for a polypeptide according to the disclosure are likewise part of the disclosure.

The disclosure likewise relates to nucleotide sequences utilizable as a primer or probe, characterized in that said sequences are selected from the nucleotide sequences according to the disclosure.

It is well understood that the present disclosure, in various embodiments, likewise relates to specific polypeptides of *Alicyclobacillus acidocaldarius*, encoded by nucleotide sequences, capable of being obtained by purification from natural polypeptides, by genetic recombination or by chemical synthesis by procedures well known to the person skilled in the art and such as described in particular below. In the same manner, the labeled or unlabeled mono- or polyclonal antibodies directed against said specific polypeptides encoded by said nucleotide sequences are also encompassed by the disclosure.

Embodiments of the disclosure additionally relate to the use of a nucleotide sequence according to the disclosure as a primer or probe for the detection and/or the amplification of nucleic acid sequences.

The nucleotide sequences according to embodiments of the disclosure can thus be used to amplify nucleotide sequences, especially by the PCR technique (polymerase chain reaction) (Erlich, 1989; Innis et al., 1990; Rolfs et al., 1991; and White et al., 1997).

These oligodeoxyribonucleotide or oligoribonucleotide primers advantageously have a length of at least 8 nucleotides, preferably of at least 12 nucleotides, and even more preferentially at least 20 nucleotides.

Other amplification techniques of the target nucleic acid can be advantageously employed as alternatives to PCR.

The nucleotide sequences of the disclosure, in particular the primers according to the disclosure, can likewise be employed in other procedures of amplification of a target nucleic acid, such as: the TAS technique (Transcription-based Amplification System), described by Kwoh et al. in 1989; the 3SR technique (Self-Sustained Sequence Replication), described by Guatelli et al. in 1990; the NASBA technique (Nucleic Acid Sequence Based Amplification), described by Kievitis et al. in 1991; the SDA technique (Strand Displacement Amplification) (Walker et al., 1992); the TMA technique (Transcription Mediated Amplification).

The polynucleotides of the disclosure can also be employed in techniques of amplification or of modification of the nucleic acid serving as a probe, such as: the LCR technique (Ligase Chain Reaction), described by Landegren et al. in 1988 and improved by Barany et al. in 1991, which employs a thermostable ligase; the RCR technique (Repair Chain Reaction), described by Segev in 1992; the CPR technique (Cycling Probe Reaction), described by Duck et al. in 1990; the amplification technique with Q-beta replicase, described by Miele et al. in 1983 and especially improved by Chu et al. in 1986, Lizardi et al. in 1988, then by Burg et al., as well as by Stone et al. in 1996.

In the case where the target polynucleotide to be detected is possibly an RNA, for example, an mRNA, it will be possible to use, prior to the employment of an amplification reaction with the aid of at least one primer according to the invention or to the employment of a detection procedure with the aid of at least one probe of the disclosure, an enzyme of reverse transcriptase type in order to obtain a cDNA from the RNA contained in the biological sample. The cDNA obtained will thus serve as a target for the primer(s) or the probe(s) employed in the amplification or detection procedure according to the disclosure.

The detection probe will be chosen in such a manner that it hybridizes with the target sequence or the amplicon generated from the target sequence. By way of sequence, such a probe will advantageously have a sequence of at least 12 nucleotides, in particular of at least 20 nucleotides, and preferably of at least 100 nucleotides.

Embodiments of the disclosure also comprise the nucleotide sequences utilizable as a probe or primer according to the disclosure, characterized in that they are labeled with a radioactive compound or with a nonradioactive compound.

The unlabeled nucleotide sequences can be used directly as probes or primers, although the sequences are generally labeled with a radioactive element ($^{32}P$, $^{35}S$, $^{3}H$, $^{125}I$) or with a nonradioactive molecule (biotin, acetylaminofluorene, digoxigenin, 5-bromodeoxyuridine, fluorescein) to obtain probes which are utilizable for numerous applications.

Examples of nonradioactive labeling of nucleotide sequences are described, for example, in French Patent No. 7810975 or by Urdea et al. or by Sanchez-Pescador et al. in 1988.

In the latter case, it will also be possible to use one of the labeling methods described in patents FR-2 422 956 and FR-2 518 755.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe).

The disclosure, in various embodiments, likewise comprises the nucleotide sequences according to the disclosure, characterized in that they are immobilized on a support, covalently or noncovalently.

According to another advantageous mode of employing nucleotide sequences according to the disclosure, the latter can be used immobilized on a support and can thus serve to capture, by specific hybridization, the target nucleic acid obtained from the biological sample to be tested. If necessary, the solid support is separated from the sample and the hybridization complex formed between said capture probe and the target nucleic acid is then detected with the aid of a second probe, a so-called "detection probe," labeled with an easily detectable element.

Another aspect of the present disclosure is a vector for the cloning and/or expression of a sequence, characterized in that it contains a nucleotide sequence according to the invention.

The vectors according to the disclosure, characterized in that they contain the elements enabling the expression and/or the secretion of said nucleotide sequences in a determined host cell, are likewise part of the disclosure.

The vector may then contain a promoter, signals of initiation and termination of translation, as well as appropriate regions of regulation of transcription. It may be able to be maintained stably in the host cell and can optionally have particular signals specifying the secretion of the translated protein. These different elements may be chosen as a function of the host cell used. To this end, the nucleotide sequences according to the disclosure may be inserted into autonomous replication vectors within the chosen host, or integrated vectors of the chosen host.

Such vectors will be prepared according to the methods currently used by the person skilled in the art, and it will be possible to introduce the clones resulting therefrom into an appropriate host by standard methods, such as, for example, lipofection, electroporation, and thermal shock.

The vectors according to the disclosure are, for example, vectors of plasmid or viral origin. One example of a vector for the expression of polypeptides of the disclosure is baculovirus.

These vectors are useful for transforming host cells in order to clone or to express the nucleotide sequences of the disclosure.

The invention likewise comprises the host cells transformed by a vector according to the disclosure.

These cells can be obtained by the introduction into host cells of a nucleotide sequence inserted into a vector such as defined above, then the culturing of said cells under conditions allowing the replication and/or expression of the transfected nucleotide sequence.

The host cell can be selected from prokaryotic or eukaryotic systems, such as, for example, bacterial cells (Olins and Lee, 1993), but likewise yeast cells (Buckholz, 1993), as well as plant cells, such as *Arabidopsis* sp., and animal cells, in particular the cultures of mammalian cells (Edwards and Aruffo, 1993), for example, Chinese hamster ovary (CHO) cells, but likewise the cells of insects in which it is possible to use procedures employing baculoviruses, for example, Sf9 insect cells (Luckow, 1993).

Embodiments of the disclosure likewise relate to organisms comprising one of said transformed cells according to the disclosure.

The obtainment of transgenic organisms according to the disclosure overexpressing one or more of the genes of *Alicyclobacillus acidocaldarius* or part of the genes may be carried out in, for example, rats, mice, or rabbits according to methods well known to the person skilled in the art, such as by viral or nonviral transfections. It will be possible to obtain the transgenic organisms overexpressing one or more of said genes by transfection of multiple copies of said genes under the control of a strong promoter of ubiquitous nature, or selective for one type of tissue. It will likewise be possible to obtain the transgenic organisms by homologous recombination in embryonic cell strains, transfer of these cell strains to embryos, selection of the affected chimeras at the level of the reproductive lines, and growth of said chimeras.

The transformed cells as well as the transgenic organisms according to the disclosure are utilizable in procedures for preparation of recombinant polypeptides.

It is today possible to produce recombinant polypeptides in a relatively large quantity by genetic engineering using the cells transformed by expression vectors according to the disclosure or using transgenic organisms according to the disclosure.

The procedures for preparation of a polypeptide of the disclosure in recombinant form, characterized in that they employ a vector and/or a cell transformed by a vector according to the disclosure and/or a transgenic organism comprising one of said transformed cells according to the disclosure are themselves comprised in the present disclosure.

As used herein, "transformation" and "transformed" relate to the introduction of nucleic acids into a cell, whether prokaryotic or eukaryotic. Further, "transformation" and "transformed," as used herein, need not relate to growth control or growth deregulation.

Among said procedures for preparation of a polypeptide of the disclosure in recombinant form, the preparation procedures include employing a vector, and/or a cell transformed by said vector and/or a transgenic organism comprising one of said transformed cells, containing a nucleotide sequence according to the disclosure of coding for a polypeptide of *Alicyclobacillus acidocaldarius*.

A variant according to the disclosure may consist of producing a recombinant polypeptide fused to a "carrier" protein (chimeric protein). The advantage of this system is that it may enable stabilization of and/or a decrease in the proteolysis of the recombinant product, an increase in the solubility in the course of renaturation in vitro and/or a simplification of the purification when the fusion partner has an affinity for a specific ligand.

More particularly, the disclosure relates to a procedure for preparation of a polypeptide of the invention comprising the following acts: a) culture of transformed cells under conditions allowing the expression of a recombinant polypeptide of a nucleotide sequence according to the disclosure; and b) if need be, recovery of said recombinant polypeptide.

When the procedure for preparation of a polypeptide of the disclosure employs a transgenic organism according to the disclosure, the recombinant polypeptide is then extracted from said organism.

The disclosure also relates to a polypeptide, which is capable of being obtained by a procedure of the disclosure, such as described previously.

The disclosure also comprises a procedure for preparation of a synthetic polypeptide, characterized in that it uses a sequence of amino acids of polypeptides according to the disclosure.

The disclosure likewise relates to a synthetic polypeptide obtained by a procedure according to the disclosure.

The polypeptides according to the disclosure can likewise be prepared by techniques, which are conventional in the field of the synthesis of peptides. This synthesis can be carried out in homogeneous solution or in solid phase.

For example, recourse can be made to the technique of synthesis in homogeneous solution described by Houben-Weyl in 1974.

This method of synthesis consists in successively condensing, two-by-two, the successive amino acids in the order required, or in condensing amino acids and fragments formed previously and already containing several amino acids in the appropriate order, or alternatively several fragments previously prepared in this way, it being understood that it will be necessary to protect beforehand all the reactive functions carried by these amino acids or fragments, with the exception of amine functions of one and carboxyls of the other or vice-versa, which must normally be involved in the formation of peptide bonds, especially after activation of the carboxyl function, according to the methods well known in the synthesis of peptides.

Recourse may also be made to the technique described by Merrifield.

To make a peptide chain according to the Merrifield procedure, recourse is made to a very porous polymeric resin, on which is immobilized the first C-terminal amino acid of the chain. This amino acid is immobilized on a resin through its carboxyl group and its amine function is protected. The amino acids that are going to form the peptide chain are thus immobilized, one after the other, on the amino group, which is deprotected beforehand each time, of the portion of the peptide chain already formed, and which is attached to the resin. When the whole of the desired peptide chain has been formed, the protective groups of the different amino acids forming the peptide chain are eliminated and the peptide is detached from the resin with the aid of an acid.

The disclosure additionally relates to hybrid polypeptides having at least one polypeptide according to the disclosure, and a sequence of a polypeptide capable of inducing an immune response in man or animals.

Advantageously, the antigenic determinant is such that it is capable of inducing a humoral and/or cellular response.

It will be possible for such a determinant to comprise a polypeptide according to the disclosure in a glycosylated, pegylated, and/or otherwise post-translationally modified form used with a view to obtaining immunogenic compositions capable of inducing the synthesis of antibodies directed against multiple epitopes.

These hybrid molecules can be formed, in part, of a polypeptide carrier molecule or of fragments thereof according to the disclosure, associated with a possibly immunogenic part, in particular an epitope of the diphtheria toxin, the tetanus toxin, a surface antigen of the hepatitis B virus (patent FR 79 21811), the VP1 antigen of the poliomyelitis virus or any other viral or bacterial toxin or antigen.

The procedures for synthesis of hybrid molecules encompass the methods used in genetic engineering for constructing hybrid nucleotide sequences coding for the polypeptide sequences sought. It will be possible, for example, to refer advantageously to the technique for obtainment of genes coding for fusion proteins described by Minton in 1984.

Said hybrid nucleotide sequences coding for a hybrid polypeptide as well as the hybrid polypeptides according to the disclosure characterized in that they are recombinant polypeptides obtained by the expression of said hybrid nucleotide sequences are likewise part of the disclosure.

The disclosure likewise comprises the vectors characterized in that they contain one of said hybrid nucleotide sequences. The host cells transformed by said vectors, the transgenic organisms comprising one of said transformed cells as well as the procedures for preparation of recombinant polypeptides using said vectors, said transformed cells and/or said transgenic organisms are, of course, likewise part of the disclosure.

The polypeptides according to the disclosure, the antibodies according to the disclosure described below and the nucleotide sequences according to the disclosure can advantageously be employed in procedures for the detection and/or identification of *Alicyclobacillus acidocaldarius*, in a sample capable of containing them. These procedures, according to the specificity of the polypeptides, the antibodies and the nucleotide sequences according to the invention which will be used, will in particular be able to detect and/or to identify an *Alicyclobacillus acidocaldarius*.

The polypeptides according to the disclosure can advantageously be employed in a procedure for the detection and/or the identification of *Alicyclobacillus acidocaldarius* in a sample capable of containing them, characterized in that it comprises the following acts: a) contacting of this sample with a polypeptide or one of its fragments according to the disclosure (under conditions allowing an immunological reaction between said polypeptide and the antibodies possibly present in the biological sample); and b) demonstration of the antigen-antibody complexes possibly formed.

Any conventional procedure can be employed for carrying out such a detection of the antigen-antibody complexes possibly formed.

By way of example, a preferred method brings into play immunoenzymatic processes according to the ELISA technique, by immunofluorescence, or radioimmunological assay processes (RIA) or their equivalent.

Thus, the disclosure likewise relates to the polypeptides according to the disclosure, labeled with the aid of an adequate label such as of the enzymatic, fluorescent or radioactive type.

Such methods comprise, for example, the following acts: deposition of determined quantities of a polypeptide composition according to the disclosure in the wells of a microtiter plate, introduction into said wells of increasing dilutions of serum, or of a biological sample other than that defined previously, having to be analyzed, incubation of the microplate, introduction into the wells of the microtiter plate of labeled antibodies directed against pig immunoglobulins, the labeling of these antibodies having been carried out with the aid of an enzyme selected from those which are capable of hydrolyzing a substrate by modifying the absorption of the radiation of the latter, at least at a determined wavelength, for example, at 550 nm, detection, by comparison with a control test, of the quantity of hydrolyzed substrate.

The polypeptides according to the disclosure enable monoclonal or polyclonal antibodies to be prepared which are characterized in that they specifically recognize the polypeptides according to the disclosure. It will advantageously be possible to prepare the monoclonal antibodies from hybridomas according to the technique described by Köhler and Milstein in 1975. It will be possible to prepare the polyclonal antibodies, for example, by immunization of an animal, in particular a mouse, with a polypeptide or a DNA, according to the disclosure, associated with an adjuvant of the immune response, and then purification of the specific antibodies contained in the serum of the immunized animals on an affinity column on which the polypeptide which has served as an antigen has previously been immobilized. The polyclonal antibodies according to the disclosure can also be prepared by purification, on an affinity column on which a polypeptide according to the disclosure has previously been immobilized, of the antibodies contained in the serum of an animal immunologically challenged by *Alicyclobacillus acidocaldarius*, or a polypeptide or fragment according to the disclosure.

The disclosure likewise relates to mono- or polyclonal antibodies or their fragments, or chimeric antibodies, characterized in that they are capable of specifically recognizing a polypeptide according to the disclosure.

It will likewise be possible for the antibodies of the disclosure to be labeled in the same manner as described previously for the nucleic probes of the disclosure, such as a labeling of enzymatic, fluorescent or radioactive type.

The disclosure is additionally directed at a procedure for the detection and/or identification of *Alicyclobacillus acidocaldarius* in a sample, characterized in that it comprises the following acts: a) contacting of the sample with a mono- or polyclonal antibody according to the disclosure (under conditions allowing an immunological reaction between said antibodies and the polypeptides of *Alicyclobacillus acidocaldarius* possibly present in the biological sample); and b) demonstration of the antigen-antibody complex possibly formed.

The present disclosure likewise relates to a procedure for the detection and/or the identification of *Alicyclobacillus acidocaldarius* in a sample, characterized in that it employs a nucleotide sequence according to the disclosure.

More particularly, the disclosure relates to a procedure for the detection and/or the identification of *Alicyclobacillus acidocaldarius* in a sample, characterized in that it includes the following acts: a) if need be, isolation of the DNA from the sample to be analyzed; b) specific amplification of the DNA of the sample with the aid of at least one primer, or a pair of primers, according to the disclosure; and c) demonstration of the amplification products.

These can be detected, for example, by the technique of molecular hybridization utilizing a nucleic probe according to the invention. This probe will advantageously be labeled with a nonradioactive (cold probe) or radioactive element.

For the purposes of the present disclosure, "DNA of the biological sample" or "DNA contained in the biological sample" will be understood as meaning either the DNA present in the biological sample considered, or possibly the cDNA obtained after the action of an enzyme of reverse transcriptase type on the RNA present in said biological sample.

A further embodiment of the disclosure comprises a method, characterized in that it comprises the following acts: a) contacting of a nucleotide probe according to the disclosure with a biological sample, the DNA contained in the biological sample having, if need be, previously been made accessible to hybridization under conditions allowing the hybridization of the probe with the DNA of the sample; and b) demonstration of the hybrid formed between the nucleotide probe and the DNA of the biological sample.

The present disclosure also relates to a procedure according to the disclosure, characterized in that it comprises the following acts: a) contacting of a nucleotide probe immobilized on a support according to the disclosure with a biological sample, the DNA of the sample having, if need be, previously been made accessible to hybridization, under conditions allowing the hybridization of the probe with the DNA of the sample; b) contacting of the hybrid formed between the nucleotide probe immobilized on a support and the DNA contained in the biological sample, if need be after elimination of the DNA of the biological sample which has not hybridized with the probe, with a nucleotide probe labeled according to the disclosure; and c) demonstration of the novel hybrid formed in act b).

According to an advantageous embodiment of the procedure for detection and/or identification defined previously, this is characterized in that, prior to act a), the DNA of the biological sample is first amplified with the aid of at least one primer according to the disclosure.

Further embodiments of the disclosure comprise methods of at least partially degrading, cleaving, and/or removing a polysaccharide, lignocellulose, hemicellulose, lignin, chitin, heteroxylan, and/or xylan-decorating group. Degrading, cleaving, and/or removing these structures have in the art recognized utility such as those described in Mielenz 2001; Jeffries 1996; Shallom and Shoham 2003; Lynd et al. 2002; Vieille and Zeikus 2001; Bertoldo et al. 2004; and/or Malherbe and Cloete 2002.

Embodiments of methods include placing a recombinant, purified, and/or isolated polypeptide having at least 90% sequence identity to SEQ ID No. 2 in fluid contact with a polysaccharide, lignocellulose, hemicellulose, lignin, chitin, heteroxylan, and/or xylan-decorating group.

Further embodiments of methods include placing a cell producing or encoding a recombinant, purified, and/or isolated polypeptide having at least 90% sequence identity to SEQ ID No. 2 in fluid contact with a polysaccharide, lignocellulose, hemicellulose, lignin, chitin, heteroxylan, and/or xylan-decorating group.

As used herein, "partially degrading" relates to the rearrangement or cleavage of chemical bonds in the target structure.

In additional embodiments, methods of at least partially degrading, cleaving, and/or removing a polysaccharide, lignocellulose, hemicellulose, lignin, chitin, heteroxylan, and/or xylan-decorating group may take place at temperatures at or above about 25, 30, 35, 40, 45, 50, 55, 60, 65, 70, 75, 80, 85, 90, and/or 95 degrees Celsius and/or at a pH at, below, and/or above 7, 6, 5, 4, 3, 2, 1, and/or 0.

Further embodiments of the disclosure may comprise a kit for at least partially degrading, cleaving, and/or removing a polysaccharide, lignocellulose, hemicellulose, lignin, chitin, heteroxylan, and/or xylan-decorating group, the kit comprising a cell producing or encoding a recombinant, purified, and/or isolated a polypeptide having at least 90% sequence identity to SEQ ID No. 2 and/or a recombinant, purified, and/or isolated a polypeptide having at least 90% sequence identity to SEQ ID No. 2.

The disclosure is described in additional detail in the following illustrative example. Although the example may represent only a selected embodiment of the disclosure, it should be understood that the following example is illustrative and not limiting.

In embodiments of the disclosure any one of the isolated and/or purified polypeptides according to the disclosure may be enzymatically active at temperatures at or above about 25, 30, 35, 40, 45, 50, 55, 60, 65, 70, 75, 80, 85, 90, and/or 95 degrees Celsius and/or may be enzymatically active at a pH at, below, and/or above 7, 6, 5, 4, 3, 2, 1, and/or 0. In further embodiments of the disclosure, glycosylation, pegylation, and/or other post-translational modification may be required for the isolated and/or purified polypeptides according to the invention to be enzymatically active at pH at or below 7, 6, 5, 4, 3, 2, 1, and/or 0 or at temperatures at or above about 25, 30, 35, 40, 45, 50, 55, 60, 65, 70, 75, 80, 85, 90, and/or 95 degrees Celsius.

All references, including publications, patents, and patent applications, cited herein are hereby incorporated by reference to the same extent as if each reference were individually and specifically indicated to be incorporated by reference and were set forth in its entirety herein.

While this disclosure has been described in the context of certain embodiments, the present disclosure can be further modified. This application therefore encompasses any variations, uses, or adaptations of the disclosure using its general principles. Further, this application encompasses such departures from the present disclosure as come within known or customary practice in the art to which this disclosure pertains and which fall within the limits of the appended claims and their legal equivalents.

EXAMPLE

Example: RAAC02760: An Acetylxylan Esterase

Provided in SEQ ID NO:1 is a nucleotide sequence isolated from *Alicyclobacillus acidocaldarius* and encoding the polypeptide of SEQ ID NO:2. As can be seen in FIGS. 1A and 1B, SEQ ID NO:2 aligns well with other proteins identified as esterases. Of particular importance, it is noted that where amino acids are conserved in other esterases, those amino acids are generally conserved in SEQ ID NO:2. Thus, the polypeptide provided in SEQ ID NO:2 is properly classified as an acetylxylan esterase.

The polypeptides of SEQ ID NOs:13-17 are representative examples of conservative substitutions in the polypeptide of SEQ ID NO:2 and are encoded by nucleotide sequences of SEQ ID NOs:8-12, respectively.

The nucleotide sequences of SEQ ID NOs:1 and 8-12 are placed into expression vectors using techniques standard in the art. The vectors are then provided to cells such as bacteria cells or eukaryotic cells such as 519 cells or CHO cells. In conjunction with the normal machinery present in the cells, the vectors comprising SEQ ID NOs: 1 and 8-12 produce the polypeptides of SEQ ID NOs: 2 and 13-17. The polypeptides of SEQ ID NOs: 2 and 13-17 are then isolated and/or purified. The isolated and/or purified polypeptides of SEQ ID NOs: 2 and 13-17 are then demonstrated to have activity as acetylxylan esterases.

The isolated and/or purified polypeptides of SEQ ID NOs: 2 and 13-17 are challenged with xylan or xylo-oligosaccharide. The isolated and/or purified polypeptides of SEQ ID NOs: 2 and 13-17 are demonstrated to have activity as acetylxylan esterases.

FIG. 2 represents the activity of four different preparations of SEQ ID NO: 2. Therein, the activity (units/mg) as an acetylxylan esterase is shown at 10, 15, and 20 minutes.

What is claimed is:

1. A method of deacetylating xylans or xylo-oligosaccharides, the method comprising:
    translating a nucleic acid sequence encoding a polypeptide having at least 90% sequence identity to the polypeptide of SEQ ID No. 2 to produce the polypeptide, and
    placing the polypeptide in fluid contact with a xylan or xylo-oligosaccharide;
    wherein the polypeptide has acetylxylan esterase activity.

2. The method according to claim 1, wherein placing the polypeptide in fluid contact with a xylan or xylo-oligosaccharide occurs at or below about pH 4.

3. The method according to claim 1, wherein placing the polypeptide in fluid contact with a xylan or xylo-oligosaccharide occurs at a temperature at or above 50 degrees Celsius.

4. The method according to claim 1, wherein the polypeptide is glycosylated, pegylated, or otherwise post-translationally modified.

5. The method according to claim 1, wherein the nucleic acid sequence comprises a nucleotide sequence having at least 90% identity to SEQ ID No. 1.

6. A method of deacetylating xylans or xylo-oligosaccharides, the method comprising:

placing a polypeptide having at least 90% sequence identity to SEQ ID NO. 2 in fluid contact with a xylan or xylo-oligosaccharide;

wherein the polypeptide has acetylxylan esterase activity.

7. The method according to claim 6, wherein placing the polypeptide in fluid contact with a xylan or xylo-oligosaccharide occurs at or below about pH 4.

8. The method according to claim 6, wherein placing the polypeptide in fluid contact with a xylan or xylo-oligosaccharide occurs at a temperature at or above 50 degrees Celsius.

9. The method according to claim 6, wherein the polypeptide is glycosylated, pegylated, or otherwise post-translationally modified.

10. The method according to claim 6, wherein the polypeptide comprises SEQ ID No. 2.

* * * * *

UNITED STATES PATENT AND TRADEMARK OFFICE
CERTIFICATE OF CORRECTION

PATENT NO. : 9,862,981 B2
APPLICATION NO. : 15/152304
DATED : January 9, 2018
INVENTOR(S) : Vicki S Thompson et al.

It is certified that error appears in the above-identified patent and that said Letters Patent is hereby corrected as shown below:

In the Specification

Column 1, Line 10, change "DE-AC07-991D13727 and" to --DE-AC07-99ID13727 and--
Column 1, Line 11, change "DE-AC07-051D14517 awarded" to --DE-AC07-05ID14517 awarded--
Column 18, Line 30, change "such as 519 cells" to --such as Sf9 cells--

Signed and Sealed this
Twenty-fourth Day of April, 2018

Andrei Iancu
*Director of the United States Patent and Trademark Office*

SEQUENCE LISTING

```
<160> NUMBER OF SEQ ID NOS: 17

<210> SEQ ID NO 1
<211> LENGTH: 618
<212> TYPE: DNA
<213> ORGANISM: Alicyclobacillus acidocaldarius

<400> SEQUENCE: 1
gtgaaggagg accttcgctt gcagcgccaa acgcccgaac cctcgtcgcc cccgcgtcac      60
ctcgccatca ccttcgacga cggcccagac ggggacatga cgcccaagat cctgtccacg     120
ctccgggatt acggcgtgcc cgccaccttt ttctgcatcg gccagcaagt cgaacgattt     180
cccgatgtcc tcaaatccat ccaccaggcc gggcacgaga tcggcaacca caccatgacc     240
catccctacc tcacgaaatt gacggacgcc gagatcgaac gggaattgcg cgaatgccaa     300
gcggccattg agaaggtcgt gcaggtgccc atccgctact ttcgcccgcc gtacggagac     360
```

```
atcgacgatc gcgtccgccg catcgcggcc tcccttcact acgaagtcgt cctctgggac    420
gtcgactcgc tcgattggtc tgggattccc ggcccagccg tcgcggccaa cgtgctgccc    480
aagctcaggc cgggcgccat catcctgatg cacgccgggc cgtttgcgaa gggtacgccg    540
gaggcgctcc cgtacgtgct cgaggtggcg gtggcaatgg gctacgattt cgtcccgctc    600
gcgaagcttc accggtga                                                  618
```

```
<210> SEQ ID NO 2
<211> LENGTH: 205
<212> TYPE: PRT
<213> ORGANISM: Alicyclobacillus acidocaldarius

<400> SEQUENCE: 2

Met Lys Glu Asp Leu Arg Leu Gln Arg Gln Thr Pro Glu Pro Ser Ser
1               5                   10                  15

Pro Pro Arg His Leu Ala Ile Thr Phe Asp Asp Gly Pro Asp Gly Asp
            20                  25                  30

Met Thr Pro Lys Ile Leu Ser Thr Leu Arg Asp Tyr Gly Val Pro Ala
        35                  40                  45

Thr Phe Phe Cys Ile Gly Gln Gln Val Glu Arg Phe Pro Asp Val Leu
    50                  55                  60

Lys Ser Ile His Gln Ala Gly His Glu Ile Gly Asn His Thr Met Thr
65                  70                  75                  80

His Pro Tyr Leu Thr Lys Leu Thr Asp Ala Glu Ile Glu Arg Glu Leu
                85                  90                  95

Arg Glu Cys Gln Ala Ala Ile Glu Lys Val Val Gln Val Pro Ile Arg
            100                 105                 110

Tyr Phe Arg Pro Pro Tyr Gly Asp Ile Asp Asp Arg Val Arg Arg Ile
        115                 120                 125

Ala Ala Ser Leu His Tyr Glu Val Val Leu Trp Asp Val Asp Ser Leu
    130                 135                 140

Asp Trp Ser Gly Ile Pro Gly Pro Ala Val Ala Ala Asn Val Leu Pro
145                 150                 155                 160

Lys Leu Arg Pro Gly Ala Ile Ile Leu Met His Ala Gly Pro Phe Ala
                165                 170                 175

Lys Gly Thr Pro Glu Ala Leu Pro Tyr Val Leu Glu Val Ala Val Ala
            180                 185                 190

Met Gly Tyr Asp Phe Val Pro Leu Ala Lys Leu His Arg
        195                 200                 205

<210> SEQ ID NO 3
<211> LENGTH: 206
<212> TYPE: PRT
<213> ORGANISM: Brevibacillus choshinensis

<400> SEQUENCE: 3

Met Glu Arg Ser Thr Pro Ile Ser Arg Arg Pro Lys Ala Val Ala Leu
1               5                   10                  15

Thr Phe Asp Asp Gly Pro Asp Gln Ile Trp Thr Pro Arg Ile Leu Asp
            20                  25                  30

Val Leu Ala Asp Tyr Arg Ile His Ala Thr Phe Met Cys Val Gly Lys
        35                  40                  45

Ala Val Gln Arg Asn Pro Gln Met Leu Arg Arg Ile Lys Asp Glu Gly
    50                  55                  60

His Ile Ile Gly Asn His Thr Trp Asp His Pro Asn Leu Thr Gln Leu
65                  70                  75                  80
```

-continued

Pro Leu Ser Asp Val Gln Thr Gln Val Leu Arg Thr Glu Glu Ile
                85                  90                  95

Asp Arg Val Ala Gly Val Lys Thr Arg Leu Phe Arg Pro Pro Tyr Gly
            100                 105                 110

Asp Leu Asn Asp Ile Val Arg Lys Val Thr Ser Leu Asp His Glu
        115                 120                 125

Ile Leu Leu Trp Asp Ile Asp Ser Trp Asp Trp Lys Gly Leu Thr Gly
    130                 135                 140

Pro Gln Val Ala Lys Asn Ile Leu Gly His Val Arg Asp Gly Ser Ile
145                 150                 155                 160

Val Leu Gln His Cys Ala Gly Pro Thr Glu Thr Val Lys Gly Thr Leu
                165                 170                 175

Glu Ala Leu Pro Tyr Ile Ile Glu Val Leu Ser Glu Ser Gly Phe Thr
            180                 185                 190

Phe Ser Thr Ile Pro Gln Leu Leu His Leu Ser Ala Tyr Arg
        195                 200                 205

<210> SEQ ID NO 4
<211> LENGTH: 208
<212> TYPE: PRT
<213> ORGANISM: Alicyclobacillus herbarius

<400> SEQUENCE: 4

Met Gln Thr Asp Ala Gln Ser Arg Val Val Arg Ile Asp Arg Pro
1               5                   10                  15

Thr Leu Thr Leu Thr Phe Asp Asp Gly Pro Asp Ala Asp Tyr Thr Pro
                20                  25                  30

Gln Ile Leu Ala Ile Leu His His Tyr Ser Val Ser Ala Thr Phe Phe
            35                  40                  45

Cys Leu Gly Gln Gln Ile Asp Gln Cys Pro His Ile Leu Lys Gln Ile
        50                  55                  60

Ala Ala Ala Gly His Thr Val Gly Asn His Ser Tyr Ser His Pro Asn
65              70                  75                  80

Leu Thr Glu Ile Thr Ser Gly Glu Val Leu Lys Gln Met Thr Glu Thr
                85                  90                  95

Asp Glu Arg Ile Ala Asn Glu Leu Gly Ser Arg Pro Arg Trp Met Arg
            100                 105                 110

Pro Pro Tyr Gly Ala Ile Asn Glu Asn Val Lys Ala Gln Leu Gln Glu
        115                 120                 125

Leu Gly Tyr Glu Ile Ile Leu Trp Asp Ile Asp Ser Arg Asp Trp Ala
    130                 135                 140

Gly Ile Pro Gly Pro Gln Ile Ala Arg Asn Ile Leu Ser Gln Leu Lys
145                 150                 155                 160

Pro Gly Ala Ile Ile Leu Gln His Cys Ser Lys Ser Ala Ala Gly Thr
                165                 170                 175

Val Glu Ala Leu Pro Tyr Val Ile Glu Ile Ala Leu Gly Leu Gly Tyr
            180                 185                 190

Glu Phe Thr Thr Leu Asp Ala Leu Leu Gly Gln Ser Pro Tyr Gln Asp
        195                 200                 205

<210> SEQ ID NO 5
<211> LENGTH: 200
<212> TYPE: PRT
<213> ORGANISM: Alicyclobacillus hesperidum

<400> SEQUENCE: 5

```
Met Asp Asn Ser Arg Thr Arg Gln Thr Pro Ala Arg Val Gly Thr
1               5                   10                  15

Leu Thr Ile Thr Phe Asp Asp Gly Pro Asp Ala Glu Tyr Thr Pro Gln
            20                  25                  30

Ile Leu Glu Thr Leu Arg His Tyr Gly Val Pro Ala Val Phe Phe Cys
            35                  40                  45

Ile Gly Glu Gln Val Ala Arg Tyr Pro Asp Val Leu Arg Ala Ile Asp
        50                  55                  60

Ala Ala Gly His Ala Ile Gly Asn His Thr Met Thr His Pro His Leu
65                  70                  75                  80

Thr Glu Leu Pro Asp Asp Glu Ile Arg Lys Gln Leu Thr Asp Ala Ala
                85                  90                  95

Asn Gln Ile Glu Ala Thr Ile Gly Lys Arg Pro His Leu Phe Arg Pro
            100                 105                 110

Pro Tyr Gly Asp Met Asp Glu Arg Val Glu Arg Ile Ala Arg Glu Leu
        115                 120                 125

Gly Tyr Gln Pro Val Leu Trp Asp Val Asp Ser Val Asp Trp Ser Gly
    130                 135                 140

Ile Pro Gly Pro Thr Val Ala Ala Asn Val Leu Pro His Leu Lys Pro
145                 150                 155                 160

Gly Ala Ile Val Leu Gln His Ala Gly Glu His Ala Glu Gly Thr Pro
                165                 170                 175

Ala Ala Leu Pro Tyr Ile Ile Glu Val Ala Val Ala Met Gly Tyr Asp
            180                 185                 190

Trp Val Pro Phe Thr Ser Lys Ser
        195                 200

<210> SEQ ID NO 6
<211> LENGTH: 184
<212> TYPE: PRT
<213> ORGANISM: Alicyclobacillus tengchongensis

<400> SEQUENCE: 6

Met Thr Ile Thr Phe Asp Asp Gly Pro Asp Ala Glu Tyr Thr Pro Lys
1               5                   10                  15

Ile Leu Glu Thr Leu Arg His Tyr Gly Val Pro Ala Val Phe Phe Cys
            20                  25                  30

Ile Gly Glu Gln Val Ala Arg Tyr Pro Asp Val Leu Arg Ala Ile Asp
        35                  40                  45

Ala Ala Gly His Ala Val Gly Asn His Thr Met Thr His Pro His Leu
    50                  55                  60

Thr Glu Leu Pro Asp Asp Glu Ile Arg Lys Gln Leu Thr Asp Ala Ala
65                  70                  75                  80

Asn Gln Ile Glu Ala Thr Ile Gly Lys Arg Pro His Leu Phe Arg Pro
                85                  90                  95

Pro Tyr Gly Asp Met Asp Arg Val Glu Arg Ile Ala Arg Glu Leu
            100                 105                 110

Gly Tyr Gln Pro Val Leu Trp Asp Val Asp Ser Val Asp Trp Ser Gly
        115                 120                 125

Ile Pro Gly Pro Thr Val Ala Ala Asn Val Leu Pro His Leu Lys Pro
    130                 135                 140

Gly Ala Ile Val Leu Gln His Ala Gly Gly His Ala Gln Gly Thr Pro
145                 150                 155                 160

Ala Ala Leu Pro Tyr Ile Ile Glu Val Ala Val Ala Met Gly Tyr Asp
```

165                 170                 175

Trp Val Pro Phe Thr Ser Lys Ser
            180

<210> SEQ ID NO 7
<211> LENGTH: 200
<212> TYPE: PRT
<213> ORGANISM: Alicyclobacillus tengchongensis

<400> SEQUENCE: 7

Met Asp Asn Ser Arg Thr Arg Gln Gln Thr Pro Ala Arg Val Gly His
1               5                   10                  15

Leu Thr Ile Thr Phe Asp Asp Gly Pro Asp Ala Glu Tyr Thr Pro Lys
            20                  25                  30

Ile Leu Glu Thr Leu Arg His Tyr Gly Val Pro Ala Val Phe Phe Cys
        35                  40                  45

Ile Gly Glu Gln Val Ala Arg Tyr Pro Asp Val Leu Arg Ala Ile Asp
    50                  55                  60

Ala Ala Gly His Ala Val Gly Asn His Thr Met Thr His Pro His Leu
65                  70                  75                  80

Thr Glu Leu Pro Asp Asp Glu Ile Arg Lys Gln Leu Thr Asp Ala Ala
                85                  90                  95

Asn Gln Ile Glu Ala Thr Ile Gly Lys Arg Pro His Leu Phe Arg Pro
            100                 105                 110

Pro Tyr Gly Asp Met Asp Asp Arg Val Glu Arg Ile Ala Arg Glu Leu
        115                 120                 125

Gly Tyr Gln Pro Val Leu Trp Asp Val Asp Ser Val Asp Trp Ser Gly
    130                 135                 140

Ile Pro Gly Pro Thr Val Ala Ala Asn Val Leu Pro His Leu Lys Pro
145                 150                 155                 160

Gly Ala Ile Val Leu Gln His Ala Gly Gly His Ala Gln Gly Thr Pro
                165                 170                 175

Ala Ala Leu Pro Tyr Ile Ile Glu Val Ala Val Ala Met Gly Tyr Asp
            180                 185                 190

Trp Val Pro Phe Thr Ser Lys Ser
        195                 200

<210> SEQ ID NO 8
<211> LENGTH: 618
<212> TYPE: DNA
<213> ORGANISM: Artificial Sequence
<220> FEATURE:
<223> OTHER INFORMATION: Substitution in SEQ ID NO 1

<400> SEQUENCE: 8
gtgaaggagg accttcgctt gcagcgccaa acgcccgaac cctcgtcgcc cccgcgtcac      60
ctcgccatca ccttcgacga cggcccagac ggggacatga cgcccaagat cctgtccacg     120
ctccgggatt acggcgtgcc cgccaccttt ttctgcatcg gccagcaagt cgaacgattt     180
cccgatgtcc tcaaatccat ccaccaggcc gggcacgaga tcggcaacca caccatgacc     240
catccctacc tcacgaaatt gacggacgcc gagatcgaac gggaattgcg cgaatgccaa     300
gcggccattg agaaggtcat tcaggtgccc atccgctact ttcgcccgcc gtacggagac     360
atcgacgatc gcgtccgccg catcgcggcc tcccttcact acgaagtcgt cctctgggac     420
gtcgactcgc tcgattggtc tgggattccc ggcccagccg tcgcggccaa cgtgctgccc     480
aagctcaggc cgggcgccat catcctgatg cacgccgggc cgtttgcgaa gggtacgccg     540

<210> SEQ ID NO 9
<211> LENGTH: 618
<212> TYPE: DNA
<213> ORGANISM: Artificial Sequence
<220> FEATURE:
<223> OTHER INFORMATION: Substitution in SEQ ID NO 1

<400> SEQUENCE: 9

```
gtgaaggagg accttcgctt gcagcgccaa acgcccgaac cctcgtcgcc cccgcgtcac      60
ctcgccatca ccttcgacga cggcccagac ggggacatga cgcccaagat cctgtccacg     120
ctccgggatt acggcgtgcc cgccaccttt ttctgcatcg ccagcaagt cgaacgatt      180
cccgatgtcc tcaaatccat ccaccaggcc gggcacgaga tcggcaacca ccatgacc      240
catccctacc tcacgaaatt gacggacgcc gagatcgaac gggaattgcg cgaatgccaa     300
gcggccattg agaaggtcgt gcaggtgccc atccgctact ttcgcccgcc gtacggagac     360
atcgacgatc gcgtccgccg catcgcggcc tcccttcact acgaagtcgt cctctgggac     420
gtcgactcgc tcgattggtc tgggattccc ggcccagccg tcgcggccaa cgtgctgccc     480
aagctcaggc cgggcgccat catcctgatg cacgccgggc cgtttgcgaa gggtacgccg     540
gaggcgctcc cgtacgtgct cgaggtggcg ctggcaatgg gctacgattt cgtcccgctc     600
gcgaagcttc accggtga                                                   618
```

<210> SEQ ID NO 10
<211> LENGTH: 618
<212> TYPE: DNA
<213> ORGANISM: Artificial Sequence
<220> FEATURE:
<223> OTHER INFORMATION: Substitution in SEQ ID NO 1

<400> SEQUENCE: 10

```
gtgaaggagg accttcgctt gcagcgccaa acgcccgaac cctcgtcgcc cccgcgtcac      60
ctcgccatca ccttcgacga cggcccagac ggggacatga cgcccaagat cctgtccacg     120
ctccgggatt acggcgtgcc cgccaccttt ttctgcatcg ccagcaagt cgaacgatt      180
cccgatgtcc tcaaatccat ccacgcggcc gggcacgaga tcggcaacca ccatgacc      240
catccctacc tcacgaaatt gacggacgcc gagatcgaac gggaattgcg cgaatgccaa     300
gcggccattg agaaggtcgt gcaggtgccc atccgctact ttcgcccgcc gtacggagac     360
atcgacgatc gcgtccgccg catcgcggcc tcccttcact acgaagtcgt cctctgggac     420
gtcgactcgc tcgattggtc tgggattccc ggcccagccg tcgcggccaa cgtgctgccc     480
aagctcaggc cgggcgccat catcctgatg cacgccgggc cgtttgcgaa gggtacgccg     540
gaggcgctcc cgtacgtgct cgaggtggcg gtggcaatgg gctacgattt cgtcccgctc     600
gcgaagcttc accggtga                                                   618
```

<210> SEQ ID NO 11
<211> LENGTH: 618
<212> TYPE: DNA
<213> ORGANISM: Artificial Sequence
<220> FEATURE:
<223> OTHER INFORMATION: Substitution in SEQ ID NO 1

<400> SEQUENCE: 11

```
gtgaaggagg accttcgctt gcagcgccaa acgcccgaac cctcgtcgcc cccgcgtcac      60
ctcgccatca ccttcgacga cggcccagac ggggactata cgcccaagat cctgtccacg     120
ctccgggatt acggcgtgcc cgccaccttt ttctgcatcg gccagcaagt cgaacgattt     180
cccgatgtcc tcaaatccat ccaccaggcc gggcacgaga tcggcaacca caccatgacc     240
catccctacc tcacgaaatt gacggacgcc gagatcgaac gggaattgcg cgaatgccaa     300
gcggccattg agaaggtcgt gcaggtgccc atccgctact ttcgcccgcc gtacggagac     360
atcgacgatc gcgtccgccg catcgcggcc tcccttcact acgaagtcgt cctctgggac     420
gtcgactcgc tcgattggtc tgggattccc ggcccagccg tcgcggccaa cgtgctgccc     480
aagctcaggc cgggcgccat catcctgatg cacgccgggc cgtttgcgaa gggtacgccg     540
gaggcgctcc cgtacgtgct cgaggtggcg gtggcaatgg gctacgattt cgtcccgctc     600
gcgaagcttc accggtga                                                   618
```

<210> SEQ ID NO 12
<211> LENGTH: 618
<212> TYPE: DNA
<213> ORGANISM: Artificial Sequence
<220> FEATURE:
<223> OTHER INFORMATION: Substitution in SEQ ID NO 1

<400> SEQUENCE: 12

```
gtgaaggagg accttcgctt gcagcgccaa acgcccgaac cctcgtcgcc cccgcgtcac      60
ctcgccatca ccttcgacga cggcccagac ggggacatga cgcccaagat cctgtccacg     120
ctccgggatt acggcgtgcc cgccaccttt ttctgcatcg gccagcaagt cgaacgattt     180
cccgatgtcc tcaaatccat ccaccaggcc gggcacgaga tcggcaacca caccatgacc     240
catccctacc tcacgaaatt gacggacgcc gagatcgaac gggaattgcg cgaatgccaa     300
gcggccattg agaaggtcgt gcaggtgccc atccgctact ttcgcccgcc gtacggagac     360
atcgacgatc gcgtccgccg catcgcgcgc tcccttcact acgaagtcgt cctctgggac     420
gtcgactcgc tcgattggtc tgggattccc ggcccagccg tcgcggccaa cgtgctgccc     480
aagctcaggc cgggcgccat catcctgatg cacgccgggc cgtttgcgaa gggtacgccg     540
gaggcgctcc cgtacgtgct cgaggtggcg gtggcaatgg gctacgattt cgtcccgctc     600
gcgaagcttc accggtga                                                   618
```

<210> SEQ ID NO 13
<211> LENGTH: 205
<212> TYPE: PRT
<213> ORGANISM: Artificial Sequence
<220> FEATURE:
<223> OTHER INFORMATION: Substitution in SEQ ID No:2

<400> SEQUENCE: 13

```
Met Lys Glu Asp Leu Arg Leu Gln Arg Gln Thr Pro Glu Pro Ser Ser
1               5                   10                  15

Pro Pro Arg His Leu Ala Ile Thr Phe Asp Asp Gly Pro Asp Gly Asp
                20                  25                  30

Met Thr Pro Lys Ile Leu Ser Thr Leu Arg Asp Tyr Gly Val Pro Ala
            35                  40                  45

Thr Phe Phe Cys Ile Gly Gln Gln Val Glu Arg Phe Pro Asp Val Leu
        50                  55                  60

Lys Ser Ile His Gln Ala Gly His Glu Ile Gly Asn His Thr Met Thr
65                  70                  75                  80
```

```
His Pro Tyr Leu Thr Lys Leu Thr Asp Ala Glu Ile Glu Arg Glu Leu
                85                  90                  95

Arg Glu Cys Gln Ala Ala Ile Glu Lys Val Ile Gln Val Pro Ile Arg
            100                 105                 110

Tyr Phe Arg Pro Pro Tyr Gly Asp Ile Asp Asp Arg Val Arg Arg Ile
            115                 120                 125

Ala Ala Ser Leu His Tyr Glu Val Val Leu Trp Asp Val Asp Ser Leu
        130                 135                 140

Asp Trp Ser Gly Ile Pro Gly Pro Ala Val Ala Ala Asn Val Leu Pro
145                 150                 155                 160

Lys Leu Arg Pro Gly Ala Ile Ile Leu Met His Ala Gly Pro Phe Ala
                165                 170                 175

Lys Gly Thr Pro Glu Ala Leu Pro Tyr Val Leu Glu Val Ala Val Ala
            180                 185                 190

Met Gly Tyr Asp Phe Val Pro Leu Ala Lys Leu His Arg
            195                 200                 205

<210> SEQ ID NO 14
<211> LENGTH: 205
<212> TYPE: PRT
<213> ORGANISM: Artificial Sequence
<220> FEATURE:
<223> OTHER INFORMATION: Substitution in SEQ ID NO:2

<400> SEQUENCE: 14

Met Lys Glu Asp Leu Arg Leu Gln Arg Gln Thr Pro Glu Pro Ser Ser
1               5                   10                  15

Pro Pro Arg His Leu Ala Ile Thr Phe Asp Asp Gly Pro Asp Gly Asp
                20                  25                  30

Met Thr Pro Lys Ile Leu Ser Thr Leu Arg Asp Tyr Gly Val Pro Ala
            35                  40                  45

Thr Phe Phe Cys Ile Gly Gln Gln Val Glu Arg Phe Pro Asp Val Leu
        50                  55                  60

Lys Ser Ile His Gln Ala Gly His Glu Ile Gly Asn His Thr Met Thr
65                  70                  75                  80

His Pro Tyr Leu Thr Lys Leu Thr Asp Ala Glu Ile Glu Arg Glu Leu
                85                  90                  95

Arg Glu Cys Gln Ala Ala Ile Glu Lys Val Val Gln Val Pro Ile Arg
            100                 105                 110

Tyr Phe Arg Pro Pro Tyr Gly Asp Ile Asp Asp Arg Val Arg Arg Ile
            115                 120                 125

Ala Ala Ser Leu His Tyr Glu Val Val Leu Trp Asp Val Asp Ser Leu
        130                 135                 140

Asp Trp Ser Gly Ile Pro Gly Pro Ala Val Ala Ala Asn Val Leu Pro
145                 150                 155                 160

Lys Leu Arg Pro Gly Ala Ile Ile Leu Met His Ala Gly Pro Phe Ala
                165                 170                 175

Lys Gly Thr Pro Glu Ala Leu Pro Tyr Val Leu Glu Val Ala Leu Ala
            180                 185                 190

Met Gly Tyr Asp Phe Val Pro Leu Ala Lys Leu His Arg
            195                 200                 205

<210> SEQ ID NO 15
<211> LENGTH: 205
<212> TYPE: PRT
<213> ORGANISM: Artificial Sequence
<220> FEATURE:
```

<223> OTHER INFORMATION: Substitution in Seq ID NO:2

<400> SEQUENCE: 15

```
Met Lys Glu Asp Leu Arg Leu Gln Arg Gln Thr Pro Glu Pro Ser Ser
1               5                   10                  15

Pro Pro Arg His Leu Ala Ile Thr Phe Asp Asp Gly Pro Asp Gly Asp
                20                  25                  30

Met Thr Pro Lys Ile Leu Ser Thr Leu Arg Asp Tyr Gly Val Pro Ala
            35                  40                  45

Thr Phe Phe Cys Ile Gly Gln Gln Val Glu Arg Phe Pro Asp Val Leu
        50                  55                  60

Lys Ser Ile His Ala Ala Gly His Glu Ile Gly Asn His Thr Met Thr
65                  70                  75                  80

His Pro Tyr Leu Thr Lys Leu Thr Asp Ala Glu Ile Glu Arg Glu Leu
                85                  90                  95

Arg Glu Cys Gln Ala Ala Ile Glu Lys Val Val Gln Val Pro Ile Arg
                100                 105                 110

Tyr Phe Arg Pro Pro Tyr Gly Asp Ile Asp Asp Arg Val Arg Arg Ile
            115                 120                 125

Ala Ala Ser Leu His Tyr Glu Val Val Leu Trp Asp Val Asp Ser Leu
        130                 135                 140

Asp Trp Ser Gly Ile Pro Gly Pro Ala Val Ala Ala Asn Val Leu Pro
145                 150                 155                 160

Lys Leu Arg Pro Gly Ala Ile Ile Leu Met His Ala Gly Pro Phe Ala
                165                 170                 175

Lys Gly Thr Pro Glu Ala Leu Pro Tyr Val Leu Glu Val Ala Val Ala
            180                 185                 190

Met Gly Tyr Asp Phe Val Pro Leu Ala Lys Leu His Arg
        195                 200                 205
```

<210> SEQ ID NO 16
<211> LENGTH: 205
<212> TYPE: PRT
<213> ORGANISM: Artificial Sequence
<220> FEATURE:
<223> OTHER INFORMATION: Substitution in Seq ID NO:2

<400> SEQUENCE: 16

```
Met Lys Glu Asp Leu Arg Leu Gln Arg Gln Thr Pro Glu Pro Ser Ser
1               5                   10                  15

Pro Pro Arg His Leu Ala Ile Thr Phe Asp Asp Gly Pro Asp Gly Asp
                20                  25                  30

Tyr Thr Pro Lys Ile Leu Ser Thr Leu Arg Asp Tyr Gly Val Pro Ala
            35                  40                  45

Thr Phe Phe Cys Ile Gly Gln Gln Val Glu Arg Phe Pro Asp Val Leu
        50                  55                  60

Lys Ser Ile His Gln Ala Gly His Glu Ile Gly Asn His Thr Met Thr
65                  70                  75                  80

His Pro Tyr Leu Thr Lys Leu Thr Asp Ala Glu Ile Glu Arg Glu Leu
                85                  90                  95

Arg Glu Cys Gln Ala Ala Ile Glu Lys Val Val Gln Val Pro Ile Arg
                100                 105                 110

Tyr Phe Arg Pro Pro Tyr Gly Asp Ile Asp Asp Arg Val Arg Arg Ile
            115                 120                 125

Ala Ala Ser Leu His Tyr Glu Val Val Leu Trp Asp Val Asp Ser Leu
        130                 135                 140
```

```
Asp Trp Ser Gly Ile Pro Gly Pro Ala Val Ala Ala Asn Val Leu Pro
145                 150                 155                 160

Lys Leu Arg Pro Gly Ala Ile Ile Leu Met His Ala Gly Pro Phe Ala
                165                 170                 175

Lys Gly Thr Pro Glu Ala Leu Pro Tyr Val Leu Glu Val Ala Val Ala
            180                 185                 190

Met Gly Tyr Asp Phe Val Pro Leu Ala Lys Leu His Arg
        195                 200                 205

<210> SEQ ID NO 17
<211> LENGTH: 205
<212> TYPE: PRT
<213> ORGANISM: Artificial Sequence
<220> FEATURE:
<223> OTHER INFORMATION: Substitution in Seq Id No:2

<400> SEQUENCE: 17

Met Lys Glu Asp Leu Arg Leu Gln Arg Gln Thr Pro Glu Pro Ser Ser
1               5                   10                  15

Pro Pro Arg His Leu Ala Ile Thr Phe Asp Asp Gly Pro Asp Gly Asp
                20                  25                  30

Met Thr Pro Lys Ile Leu Ser Thr Leu Arg Asp Tyr Gly Val Pro Ala
            35                  40                  45

Thr Phe Phe Cys Ile Gly Gln Gln Val Glu Arg Phe Pro Asp Val Leu
        50                  55                  60

Lys Ser Ile His Gln Ala Gly His Glu Ile Gly Asn His Thr Met Thr
65                  70                  75                  80

His Pro Tyr Leu Thr Lys Leu Thr Asp Ala Glu Ile Glu Arg Glu Leu
                85                  90                  95

Arg Glu Cys Gln Ala Ala Ile Glu Lys Val Val Gln Val Pro Ile Arg
            100                 105                 110

Tyr Phe Arg Pro Pro Tyr Gly Asp Ile Asp Asp Arg Val Arg Arg Ile
        115                 120                 125

Ala Arg Ser Leu His Tyr Glu Val Val Leu Trp Asp Val Asp Ser Leu
    130                 135                 140

Asp Trp Ser Gly Ile Pro Gly Pro Ala Val Ala Ala Asn Val Leu Pro
145                 150                 155                 160

Lys Leu Arg Pro Gly Ala Ile Ile Leu Met His Ala Gly Pro Phe Ala
                165                 170                 175

Lys Gly Thr Pro Glu Ala Leu Pro Tyr Val Leu Glu Val Ala Val Ala
            180                 185                 190

Met Gly Tyr Asp Phe Val Pro Leu Ala Lys Leu His Arg
        195                 200                 205
```